United States Patent
Laborde et al.

(10) Patent No.: US 6,962,926 B2
(45) Date of Patent: *Nov. 8, 2005

(54) ANTAGONIST OF MCP-1 FUNCTION, AND COMPOSITIONS AND METHODS OF USE THEREOF

(75) Inventors: Edgardo Laborde, Foster City, CA (US); Louise Robinson, San Carlos, CA (US); Fanying Meng, San Francisco, CA (US); Brian T. Peterson, Mountain View, CA (US); Hugo O. Villar, La Jolla, CA (US); Steven E. Anuskiewicz, San Bruno, CA (US); Wenli Ma, Mountain View, CA (US); Yukiharu Matsumoto, Gifu (JP); Kunihisa Baba, Yokkaichi (JP); Hideaki Inagaki, Inabe (JP); Katsumasa Tanaka, Inabe (JP); Yoshiro Ishiwata, Aichi-gun (JP); Shoji Yokochi, Inabe-gun (JP); Masayuki Okamoto, Tokyo-to (JP); Takashi Nakamura, Kuwana (JP); Atsushi Miyachi, Kuwana (JP); Mitsuaki Takeuchi, Inabe (JP); Kouji Matsushima, Matsudo (JP)

(73) Assignees: Telik, Inc., Palo Alto, CA (US); Sanwa Kagaku Kenkyusho Co., Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/637,746

(22) Filed: Aug. 8, 2003

(65) Prior Publication Data

US 2004/0198719 A1 Oct. 7, 2004

Related U.S. Application Data

(63) Continuation-in-part of application No. 10/060,967, filed on Jan. 29, 2002, now Pat. No. 6,670,364.
(60) Provisional application No. 60/265,841, filed on Jan. 31, 2001.

(51) Int. Cl.[7] .................. A61K 31/437; A61K 31/496; C61K 31/5377; C07D 471/04; A61P 29/00
(52) U.S. Cl. .............. 514/303; 514/217.07; 514/234.2; 514/253.04; 546/120; 546/119; 544/127; 544/362; 540/597; 540/599
(58) Field of Search .................. 514/303, 217.07, 514/234.2, 253.04; 546/120, 119; 544/127, 362; 540/597, 599

(56) References Cited

U.S. PATENT DOCUMENTS

| | | | |
|---|---|---|---|
| 3,823,144 A | 7/1974 | Schmitt et al. | ............. 544/377 |
| 4,269,990 A | 5/1981 | May et al. | .................. 548/315 |
| 5,977,108 A | 11/1999 | Kikuchi et al. | ............. 514/249 |
| 6,140,338 A | 10/2000 | Naya et al. | .................. 514/299 |
| 6,228,869 B1 | 5/2001 | Levin et al. | |
| 6,288,103 B1 | 9/2001 | Faull et al. | .................. 514/419 |
| 6,316,449 B1 | 11/2001 | Bratton et al. | ......... 514/252.04 |
| 6,326,379 B1 | 12/2001 | Macor et al. | ............... 514/303 |
| 6,329,402 B1 | 12/2001 | Kikuchi et al. | ............. 514/341 |
| 6,342,516 B1 | 1/2002 | Umeda et al. | .............. 514/397 |
| 6,670,364 B2 * | 12/2003 | Robinson et al. | ...... 514/253.04 |

FOREIGN PATENT DOCUMENTS

| | | | |
|---|---|---|---|
| FR | 2 001 284 | 9/1969 | .......... A61K/21/00 |
| GB | 1 250 611 | 10/1974 | .......... C07D/99/22 |
| JP | 9-255572 | 9/1997 | |
| WO | 92/14710 | 9/1992 | ......... C07D/211/26 |
| WO | 97/24325 | 7/1997 | |

(Continued)

OTHER PUBLICATIONS

Alam et al., "Increased MCP–1, RANTES, and MIP–1α in Bronchoalveolar Lavage Fluid of Allergic Asthmatic Patients", *Am J Respir Crit Care Med*, 153:1398–1404. (1996).

(Continued)

*Primary Examiner*—Evelyn Mei Huang
(74) *Attorney, Agent, or Firm*—Foley & Lardner LLP

(57) ABSTRACT

Compounds of formula A and formula B:

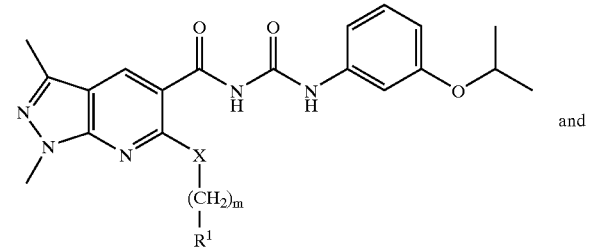

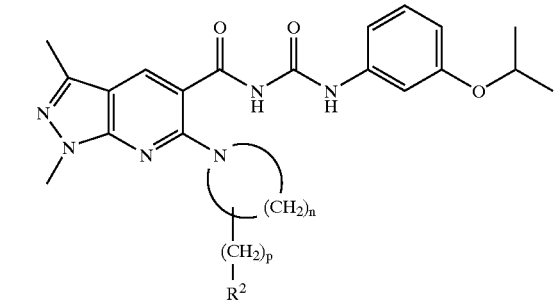

and their pharmaceutically acceptable salts, compositions comprising them, methods for their use, and their use in the preparation of medicaments. The compounds are antagonists of MCP-1 function, and are useful in the prevention and treatment of chronic or acute inflammatory or autoimmune diseases, such as multiple sclerosis, and in the prevention and treatment of allergic hypersensitivity disorders.

20 Claims, No Drawings

FOREIGN PATENT DOCUMENTS

| | | | |
|---|---|---|---|
| WO | 97/44329 | 11/1997 | |
| WO | 98/02151 | 1/1998 | |
| WO | 98/06703 | 2/1998 | |
| WO | 98/27815 | 7/1998 | |
| WO | 98/04554 | 5/1999 | |
| WO | 99/40072 | 8/1999 | ......... C07D/235/16 |
| WO | 00/46198 | 8/2000 | |
| WO | 01/36403 A1 | 5/2001 | |
| WO | 01/57003 | 8/2001 | ......... C07D/265/36 |
| WO | 01/57021 | 8/2001 | ......... C07D/401/14 |
| WO | 01/57044 | 8/2001 | |
| WO | 02/060900 A2 | 8/2002 | |

OTHER PUBLICATIONS

Alcami et al., "Blockade of Chemokine Activity by a Soluble Chemokine Binding Protein form Vaccinia Virus", *J Immunol*, 160:624–633 (1998).

Antoniades et al., "Expression of monocyte chemoattractant protein 1 mRNA in human idiopathic pulmonary fibrosis", *Proc Natl Acad Sci USA*, 89:5371–5375 (1992).

Ajuebor et al., "Endogenous monocyte chemoattractant protein–1 recruits monocytes in the zymosan peritonitis model", *Journal of Leukocyte Biology*, vol. 63:108–116, Jan. 1998.

Baggiolini et al., "Human Chemokines; an update", Annu rev Immunol (1997), pp. 15:675–705.

Baggiolini, Chemokines and Leukocyte Traffic, Nature vol: 392:9 pp 565–568, (1998).

Boring et al., "Decreased lesion formation in CCR2$^{-/-}$ mice reveals a role for chemokines in the initiation of atherosclerosis", *Nature*, 394:894–897 (1998).

Bright et al., "Identification of a Non Peptidic Rantes Antagonist", *Bioorg Med Chem Lett*, 8:771–774 (1998).

Campbell et al., "Monocyte Chemoattractant Protein–1 Mediates Cockroach Allergen–Induced Bronchial Hyperreactivity in Normal but Not CCR2$^{-/-}$ Mice: The Role of Mast Cells", J Immunol, 163:2160–2167 (1999).

Chemical Abstracts, 103(17), Abst. No. 141873u (1985); Abstract of Kuxzinski, L. et al: "Synthesis of new 4 and 5 disubstituted isothizoles"Pol J Pharmacol Pahrm, 36(5):485–491 (1984).

Chemical Abstracts, 100(21), Abst. No. 174751u (1984): Abstract of Ormek, G. et al., "Ring–opening reactions of potentially biologically active benzothienooxazines" Arc Pharm, 317(2):117–120 (1984).

Folkman and Shing, "Control of Angiogensis by Heparin and Other Sulfated Polysaccharides", *Adv Exp Med Biol.*, 313:355–364 (1992).

Forbes et al., "CCR2B Receptor Antagonists: Conversion of a Weak HTS Hit to a Potent Lead Compound", *Bioorg Med Chem. Lett*, 10:1803–1806 (2000).

Gosling et al., "MCP–1 deficiency reduces susceptibility to atherosclerosis in mice that over express human apo37lipoprotein B", *J Clin Invest*, 103:773–778 (1999).

Gu et al., "Absence of Monocyte Chemoattractant Protein–1 Reduces Atherosclerosis in Low Density Lipoprotein Receptor–Deficient Mice", *Mol Cell*, 2:275–281 (1998).

Hesselgesser, "Identification and Characterization of Small Molecule Functional Antagonists of the CCR1 Chemokine Receptor", *J. Biol Chem*, 273:15687–15692 (1998).

Hoogewerf et al., "Glycosaminoglycans Mediate Cell Surface Oligomerization of Chemokines", Biochemistry 36:13570–13578, (1997).

Hosaka et al., "Expression of the Chemokine Superfamily in Rheumatoid Arthritis", *Clin Exp Immunol*, 97:451–457. (1994).

Hsieh et al., "Immunotherapy Suppresses the Production of monocyte chemotactic and activating factor and augments the production of IL–8 in Children with Asthma", *J Allergy Clin Immunol*, 98:580–587 (1996).

Kitano M. et al., "Synthesis and Biological Activity of N–(Aminoiminomethly)–1H–Idoleca Rboxamide Inhibitors", Chem and Pharm Bulletin, Pharmaceutical Society of Japan, vol. 47, No. 11, Nov. 1999, pp 1538.

Koch et al., "Enhanced Production of Monocyte Chemoattractant Protein–1 in Rheumatoid Arthritis", *J Clin Invest*, 90:772–779, (1992).

Kunkel et al., "The Role of Chemokines in Inflammatory Joint Disease", *J Leukocyte Biol*, 59:6–12 (1996).

Kurashima et al., "Increase of Chemokine Levels in Sputum Precedes Exacerbation of Acute Asthma Attacks", *J Leukocyte Biol*, 59:313–316, (1996).

Kuschert et al., "Glycosamineoglycans interact selectively with chemokines and moldulate receptor binding and cellular responses", *Biochemistry* 38:12959–12968, (1999).

Liang et al., "Identification and characterization of a potent, selective and orally active antagonist of the cc chemokine receptor–1", *The Journal of Biological Chemistry*, vol. 25:19000–19008, Jun. 23, 2000.

Luster, "Chemokines__Chemotactic Cytokines That Mediate Inflammation", *The new England Journal of Medicine*, pp. 436–445, Feb. 12, 1998.

McFadden and Kelvin, "New Strategies for Chemokine Inhibition and Modulation", *Biochem Pharmacol*, 54:1271–1280 (1997).

Mirzadegan et al., "Identification of the binding site for a novel class of CCR2bcemokine receptor antagonists . . . ", The American Society for Biochemistry and Molecular Biology, Inc., manuscript M000692200, (2000).

Moore et al., "Tumor angiogenesis is regulated by CXC chemokines", *J. Lab Clin Med*, 132:97–103 (1998).

Moore et al., "CXC Chemokine Modulation of angiogenesis . . . ", J Investigative Medicine, vol 46:113–120 (1998).

Murphy, :The Molecular Biology of Leukocyte Chemoattractant Receptors, *Annu Rev Immun*,12:593–633,(1994).

Nelken et al., "Monocyte Chemoattractant Protein–1 in Human Atheromatous Plaques", *J. Clin Invest*, 88:1121–1127 (1991).

Okada et al., "Synthesis and Antitumor Activities of Water–Soluble Benzoylphenylureas", *Chem Pharm Bull*, 47:430–433, (1999).

Okada et al., "Synthesis and Antitumor Activities of Prodrugs of Benzoylphenylureas", *Chem Pharm Bull* 42:57–61, (1994).

Okada et al., "Synthesis and Antitumor Activities of Novel Benzoylphenylurea Derivatives", *Chem Pharm Bull*, 39:2308–2315 (1991).

Proost et al., "The Role of Chemokines in Inflammation", *Int J Clin Lab Res*, 26:211–223, (1996).

Robinson et al., "Chemokine expression in Rheumatoid Arthritis . . . ", *Clin Exp Innumol* 101:398–407 (1995).

Rollins, "Chemokines", *Blood*, vol 90 No. 3, pp. 909–928, Aug. 1, 1997.

Rousseau, Jean–Francois et al., Chemical Abstract, "Regioselective ortho–directed metalation and electrophilic substitution of indoleand indoling –5–(N–phenyl) carboxamides" retrieved from STN database accession No. 136:355126 XP002206081 abstract & Heterocycles 92001), 55(12), 2289–2304.

Rovin et al., "Chemotactic Factors and Renal Inflammation", *American Journal of Kidney Diseases*, 31:1065–1084, Jun. 1998.

Rovin, "Chemokines as Therapeutic Targets in Renal Inflammation", American Journal of Kidney Diseases, 34: 761–767, Oct. 1999.

Rovin, "Chemokine blokade as a therapy for renal disease", *Current Opinion in Nephrology and Hypertension*, 13:225–232, (2000).

Rovin et al., "A Novel Polymorphism in the MCP–1 Gene Regulatory Region That Influences MCP–1 Expression", *Biochemical and Biophysical Research Communications*, 259, pp. 344–348, (1999).

Saunders and Tarby, "Opportunities for novel therapeutic agents acting at chemokine receptors", Drug Discovery Today, vol. 4 No. 2 (1999).

Schall, "Biology of the RANTES/SIS Cytokine Family", *Cytokine*, 3:165–183, (1991).

Sendo et al., "Regulation of leukocyte adherence and migration by glycosylphosphatidyl–inositol–anchored proteins", *Journal of Leukocyte Biology*, vol. 66, pp. 369–374, Sep. 1999.

Servant et al., "Polarization of Chemoattract Receptor Signaling During Neutrophil Chemotaxis", *Science*, vol. 287: 1037–1040, Feb. 11, 2000.

Strieter et al., "The Immunopathology of Chemotactic Cytokines: The Role of Interleukin–8 and Monocyte Chemoattractant Protein–1", *J Lab Clin Med*, 123:183–197 (1994).

Sugiyama et al., "Chemokines in Brochoalveolar Lavage Fluid in Summer–type Hypersensitivity Pneumonitis", *Eur Respir J*, 8:1084–1090 (1995).

Szekanecz et al., "Cytokines in Rheumatoid Arthritis", *Drugs and Aging*, 12:377–390, May 12, 1998.

Taub, D.D. "Chemokine–Leukocyte Interactions", *Cytokine Growth Factor Rev*, 7:355–376, (1996).

Takeya et al., "Detection of Monocyte Chemoattractant Protein–1 in Human Atherosclerotic Lesions by an Anti–monocyte Chemoattractant Protein–1 Monoclonal Antibody", *Human Pathol*, 24:534–539 (1993).

Tanaka et al., "T–cell adhesion induced by proteoglycan–immobilzed cytokine MIP–1β", *Nature*, 361:79–82 (1993).

Trivedi et al., "Chemokines: Targets for novel therapeutics", *Annual Reports in Medicinal Chemistry*, 35:191–200, (2000).

Vaddi and Newton, "Comparison of biological responses of human monocytes and THP–1 cells to chemokines fo the intercrine–β family", *Journal of Leukocyte Biology*, vol 55: 756–761, Jun. 1994.

Villiger et al., "Production of Monocyte Chemoattractant Protein–1 By Inflamed Synovial Tissue and Cultered Synoviocytes", *J Immunol*, vol. 149, pp. 722–727, (1992).

Vlodavsky et al., "Involvement of heparan sulfate and related molecules in sequestration and growth promoting activity of fibroblast growth factor", *Cancer and Mtastasis Reviews* 15: 177–186,(1996).

Waltenberger et al., "Suramin is a Potent Inhibitor of Vascular Endothelial Growth Factor. A Contribution to the Molecular Basis of its Antiangiogenic Action", *J Mol Cell Cardiol*, 28:1523–1529, (1996).

Wang et al, "Chemokines and their role in tumor growth and metastasis", *Journal of Immunological Methods*, 220: 1–17, (1998).

Wellstein and Czubayko, "Inhibition of fibroblast growth factors", *Breast Cancer Res Treat*, 38:109–119 (1996).

White, "Identificaiton of a Potent, Selective Non–peptide CXCR2 Antagonist That Inhibits Interleukin–8–induced Neutrophil Migration", *J. Bio Chem*, 273:10095–10098 (1998).

Wrenshall et al., "Modulation of macrophage and B cell funtion by glycosaminoglycans", Journal of Leukocyte Biology, vol. 66:391–400, Sep. 1999.

Yang et al., "Fully human anti–interleukin–8 monoclonal antibodies: potential therapeutics for the treatment of inflammatory disease states", Journal of Leukocyte Biology, vol. 66: 401–410, Sep. 1999.

Yla–Herttuala et al., "Expression of Monocyte Chemoattractant Protein 1 in Macrophage–Rich Areas of Human and Rabbit Atheroslerotic Lesions", *Proc Natl Acad Sci USA*, 88:5252–5256 (1991).

Zetzsche et al., Crossfire Beilstein 'Online' Beilstein Institut Aur Forerderung Der Wissenschaten, Frankfurt, DE; Abstract, Chemische Berichte, vol. 72, 1939, p. 1599.

* cited by examiner

ANTAGONIST OF MCP-1 FUNCTION, AND COMPOSITIONS AND METHODS OF USE THEREOF

CROSS-REFERENCE TO RELATED APPLICATIONS

This application is a continuation-in-part of U.S. application Ser. No. 10/060,967, filed 29 Jan. 2002 now U.S. Pat. No. 6,670,364. U.S. application Ser. No. 10/060,967 claims the priority under 35 USC 119(e) of U.S. Provisional Application No. 60/265,841, filed 31 Jan. 2001. Each of these applications is incorporated into this application by reference.

BACKGROUND OF THE INVENTION

1. Field of the Invention

This invention relates to compounds that are antagonists of MCP-1 function, to compositions containing them, and to methods for their use.

2. Description of the Related Art

U.S. application Ser. No. 10/060,967 (published as PCT International Publication No. WO 02/060900 on 8 Aug. 2002 and as U.S. Patent Application Publication No. 2003/0096705 on 22 May 2003) discloses compounds of formula I and formula II:

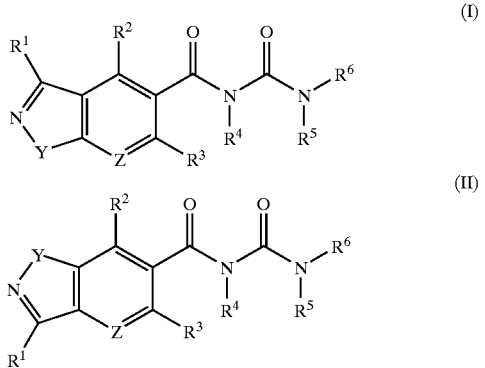

where:
Y is O, S or N—$R^7$,
Z is N or C—$R^8$,
$R^1$, $R^2$, $R^3$, and $R^8$ are independently, hydrogen, or optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —$CF_3$, halogen, nitro, —CN, —$OR^9$, —$SR^9$, —$NR^9R^{10}$, —$NR^9$(carboxy(lower alkyl)), —C(=O)$R^9$, —C(=O)O$R^9$, —C(=O)N$R^9R^{10}$, —OC(=O)$R^9$, —$SO_2R^9$, —O$SO_2R^9$, —$SO_2NR^9R^{10}$, —$NR^9SO_2R^{10}$ or —$NR^9C$(=O)$R^{10}$, wherein $R^9$ and $R^{10}$ are independently, hydrogen, optionally substituted lower alkyl, lower alkyl-N($C_{1-2}$ alkyl)$_2$, lower independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, optionally substituted aryloxy, heteroaryl, heteroaryl(lower alkyl), or $R^9$ and $R^{10}$ together are —(CH$_2$)$_{4-6}$— optionally interrupted by one O, S, NH, N-(aryl), N-(aryl(lower alkyl)), N-(carboxy(lower alkyl)) or N-(optionally substituted $C_{1-2}$ alkyl) group,
$R^7$ is hydrogen, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), —C(=O)$R^9$, —C(=O)O$R^9$, —C(=O)N$R^9R^{10}$, —$SO_2R^9$, or —$SO_2NR^9R^{10}$, wherein $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl (lower alkyl), optionally substituted heterocycloalkyl (lower alkyl), aryl(lower alkyl), optionally substituted aryl, optionally substituted aryloxy, heteroaryl, heteroaryl (lower alkyl), or $R^9$ and $R^{10}$ together are —(CH$_2$)$_{4-6}$— optionally interrupted by one O, S, NH, N-(aryl), N-(aryl (lower alkyl)), N-(carboxy(lower alkyl)) or N-(optionally substituted $C_{1-2}$ alkyl) group,
$R^4$ and $R^5$ are independently, hydrogen, lower alkyl optionally substituted lower alkyl, optionally substituted aryl, or optionally substituted aryl(lower alkyl), or, together, are —(CH$_2$)$_{2-4}$—,
$R^6$ is hydrogen, optionally substituted lower alkyl, alkenyl, alkynyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl (lower alkyl), —C(=O)$R^{11}$, —C(=O)O$R^{11}$, —C(=O)N$R^{11}R^{12}$, —$SO_2R^{11}$, or —$SO_2NR^{11}R^{12}$, wherein $R^{11}$ and $R^{12}$ are independently, hydrogen, optionally substituted lower alkyl, alkenyl, alkynyl, cycloalkyl, cycloalkyl (lower alkyl), aryl, optionally substituted aryloxy, heteroaryl, heteroaryl(lower alkyl), or $R^{11}$ and $R^{12}$ together are —(CH)$_{4-6}$—, and the pharmaceutically acceptable salts thereof, optionally in the form of single stereoisomers or mixtures of stereoisomers thereof.

The application also discloses the synthesis of these compounds, pharmaceutical compositions comprising them, and methods for their use. The compounds are described as antagonists of MCP-1 (monocyte chemoattractant protein-1, also referred to as MCAF, macrophage/monocyte chemotactic and activating factor) function, useful in the prevention and treatment of chronic or acute inflammatory or autoimmune diseases, especially those associated with aberrant lymphocyte or monocyte accumulation such as atherosclerosis, Crohn's disease, diabetic nephropathy, inflammatory bowel disease, multiple sclerosis, nephritis, pancreatitis, pulmonary fibrosis, psoriasis, restenosis, rheumatoid arthritis, and transplant rejection. The compounds are also described as useful in the prevention and treatment of allergic hypersensitivity disorders, especially those characterized by basophil activation and eosinophil recruitment such as allergic rhinitis and asthma.

SUMMARY OF THE INVENTION

In a first aspect, this invention is compounds of formula A and formula B:

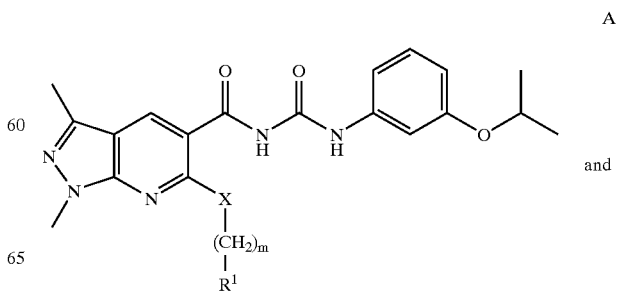

and

-continued

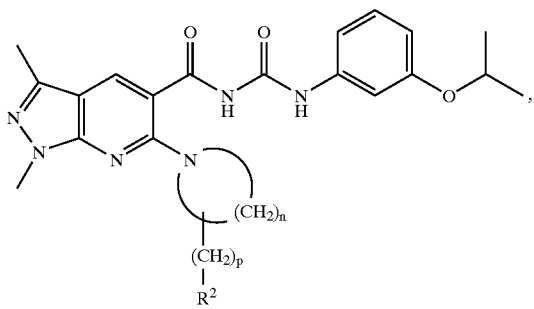

where:
m is 1, 2, or 3 (except that when X is CH$_2$, m is 1);
n is 4 or 5;
p is 0 or 1;
R$^1$ is pyrrolidin-1-yl, piperidin-1-yl, morpholin-4-yl, piperazin-1-yl, 4-methylpiperazin-1-yl, or hexahydroazepin-1-yl;
R$^2$ is dimethylamino, ethylmethylamino, diethylamino, pyrrolidin-1-yl, or piperidin-1-yl;
X is O, S, CH$_2$, NH, or N(CH$_3$);
and their pharmaceutically acceptable salts.

In a second aspect, this invention is pharmaceutical compositions comprising a compound of the first aspect of this invention, typically in a therapeutically effective amount, and a pharmaceutically acceptable excipient.

In a third aspect, this invention is methods of treating, in mammals in need thereof, diseases treatable by administering an antagonist of MCP-1 function, comprising administering to the mammal a therapeutically effective amount of a compound of the first aspect of this invention. This third aspect of the invention also includes the use of a compound of the first aspect of this invention in the preparation of a medicament for the treatment of diseases treatable by administering an antagonist of MCP-1 function. Exemplary diseases treatable by the compounds of this invention include inflammatory and autoimmune diseases such as atherosclerosis, Crohn's disease, diabetic nephropathy, inflammatory bowel disease, multiple sclerosis, nephritis, pancreatitis, pulmonary fibrosis, psoriasis, restenosis, rheumatoid arthritis, and transplant rejection; and allergic hypersensitivity disorders such as allergic rhinitis and asthma.

In a fourth aspect, this invention is methods of preparing the compounds of the first aspect of this invention.

DETAILED DESCRIPTION OF THE INVENTION

Definitions

Unless the context requires otherwise, the singular includes the plural. "Comprising" is a term of inclusion and not of limitation. Thus, a pharmaceutical composition comprising a compound of this invention and a pharmaceutically acceptable excipient may contain more than one compound of this invention, may contain an other pharmaceutically active ingredient or ingredients, and may contain more than one excipient.

A "pharmaceutically acceptable salt" means a salt that is pharmaceutically acceptable and has the desired pharmacological properties. Such salts are acid addition salts formed with inorganic acids (e.g. hydrochloric acid, hydrobromic acid, sulfuric acid (giving the sulfate and bisulfate salts), nitric acid, phosphoric acid, and the like) and organic acids (e.g. acetic acid, propionic acid, trimethylacetic acid, tert-butylacetic acid, cyclopentanepropionic acid, hexanoic acid, heptanoic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, salicylic acid, lactic acid, 3-(4-hydroxybenzoyl)benzoic acid, 3-phenylpropionic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, glucuronic acid, amino acids such as glutamic acid, 3-hydroxy-2-naphthoic acid, methanesulfonic acid, ethanesulfonic acid, 1,2-ethanedisulfonic acid, 2-hydroxyethanesulfonic acid, benzenesulfonic acid, 4-toluenesulfonic acid, 4-chlorobenzenesulfonic acid, 2-naphthalenesulfonic acid, camphorsulfonic acid, and the like).

A "pharmaceutically acceptable excipient" means an excipient that is useful in preparing a pharmaceutical composition (medicament) that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "disease" includes any unhealthy condition of an animal (which includes human and non-human mammals), including particularly inflammatory and autoimmune diseases such as atherosclerosis, Crohn's disease, diabetic nephropathy, inflammatory bowel disease, multiple sclerosis, nephritis, pancreatitis, pulmonary fibrosis, psoriasis, restenosis, rheumatoid arthritis, and transplant rejection; and allergic hypersensitivity disorders such as allergic rhinitis and asthma.

"Treating" or "treatment" of a disease in a mammal includes: preventing the disease from occurring in a mammal which may be predisposed to the disease but does not yet experience or display symptoms of the disease; inhibiting the disease, i.e. arresting its development; and relieving the disease, i.e. causing regression of the disease.

A "therapeutically effective amount" means that amount which, when administered to a mammal for treating a disease, is sufficient to effect such treatment for the disease.

The compounds and their pharmaceutically acceptable salts

In a first aspect, this invention is compounds of formula A and formula B:

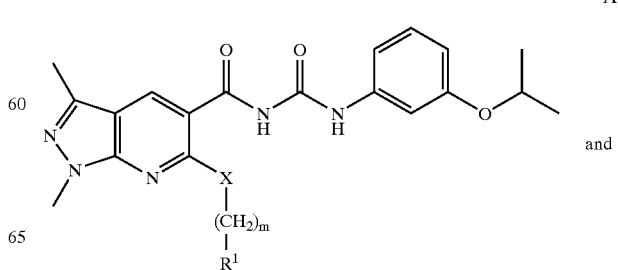

-continued

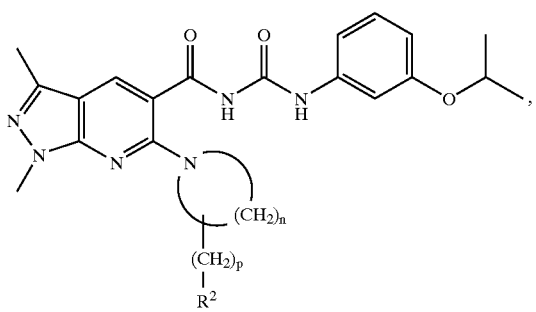

B where:
m is 1, 2, or 3 (except that when X is CH$_2$, m is 1);
n is 4 or 5;
p is 0 or 1;
R$^1$ is pyrrolidin-1-yl, piperidin-1-yl, morpholin-4-yl, piperazin-1-yl, 4-methylpiperazin-1-yl, or hexahydroazepin-1-yl;
R$^2$ is dimethylamino, ethylmethylamino, diethylamino, pyrrolidin-1-yl, or piperidin-1-yl;
X is O, CH$_2$, NH, or N(CH$_3$);
and their pharmaceutically acceptable salts.

Pharmaceutically acceptable salts of the compounds are salts which may be formed when the parent compound contains a basic group. Salts of the compounds are prepared in a suitable solvent from the compound in free base form and an excess of the acid. The free base form may be regenerated by contacting the salt with a base and isolating the free base in the conventional manner. The pharmaceutically acceptable salt forms can differ from the free base forms in certain physical properties such as increased solubility in protic solvents (e.g. water solubility).

Some of the compounds, and their salts, may exist in solvated forms, including hydrated forms, as well as in unsolvated forms; and the solvates are included within the scope of this invention. Some of the compounds, and their salts, may also exist in one or more solid or crystalline phases or polymorphs; and the polymorphs are also included within the scope of this invention.

Compounds of the invention are named in this application as derivatives of urea. Thus, the compound of the formula

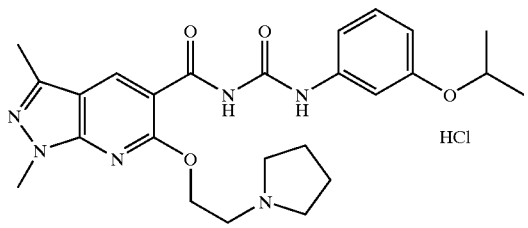

is named 1-{1,3-dimethyl-6-[2-(pyrrolidin-1-yl)ethoxy]-1H-pyrazolo[3,4-b]pyridine-5-carbonyl}-3-(3-isopropoxyphenyl)urea hydrochloride.

Preferred compounds of the invention include those in which:
(1) the compound is of formula A where X is O, NH, or N(CH$_3$); especially where m is 2;
(2) the compound is of formula A where X is CH$_2$; or
(3) the compound is of formula B.

Particular compounds of this invention are:
1-{1,3-dimethyl-6-[2-(pyrrolidin-1-yl)ethoxy]-1H-pyrazolo[3,4-b]pyridine-5-carbonyl}-3-(3-isopropoxy-phenyl)urea,
1-{1,3-dimethyl-6-[2-(piperidin-1-yl)ethoxy]-1H-pyrazolo[3,4-b]pyridine-5-carbonyl}-3-(3-isopropoxy-phenyl)urea,
1-{1,3-dimethyl-6-[2-(morpholin-4-yl)ethoxy]-1H-pyrazolo[3,4-b]pyridine-5-carbonyl}-3-(3-isopropoxy-phenyl)urea,
1-{1,3-dimethyl-6-[3-(hexahydroazepin-1-yl)propoxy]-1H-pyrazolo[3,4-b]pyridine-5-carbonyl}-3-(3-isopropoxy-phenyl)urea,
1-{1,3-dimethyl-6-[2-(pyrrolidin-1-yl)ethylamino]-1H-pyrazolo[3,4-b]pyridine-5-carbonyl}-3-(3-isopropoxy-phenyl)urea,
1-{1,3-dimethyl-6-[2-(piperidin-1-yl)ethylamino]-1H-pyrazolo[3,4-b]pyridine-5-carbonyl}-3-(3-isopropoxy-phenyl)urea,
1-{1,3-dimethyl-6-[2-(morpholin-4-yl)ethylamino]-1H-pyrazolo[3,4-b]pyridine-5-carbonyl}-3-(3-isopropoxy-phenyl)urea,
1-{1,3-dimethyl-6-[[2-(pyrrolidin-1-yl)ethyl]methylamino]-1H-pyrazolo[3,4-b]pyridine-5-carbonyl}-3-(3-isopropoxy-phenyl)urea,
1-{1,3-dimethyl-6-[[2-(piperidin-1-yl)ethyl]methylamino]-1H-pyrazolo[3,4-b]pyridine-5-carbonyl}-3-(3-isopropoxy-phenyl)urea,
1-{1,3-dimethyl-6-[4-(pyrrolidin-1-yl)piperidin-1-yl]-1H-pyrazolo[3,4-b]pyridine-5-carbonyl}-3-(3-isopropoxy-phenyl)urea,
1-{1,3-dimethyl-6-[4-(piperidin-1-yl)piperidin-1-yl]-1H-pyrazolo[3,4-b]pyridine-5-carbonyl}-3-(3-isopropoxy-phenyl)urea,
1-{1,3-dimethyl-6-[4-(dimethylamino)piperidin-1-yl]-1H-pyrazolo[3,4-b]pyridine-5-carbonyl}-3-(3-isopropoxy-phenyl)urea,
1-{1,3-dimethyl-6-[2-(pyrrolidin-1-ylmethyl)pyrrolidin-1-yl]-1H-pyrazolo[3,4-b]pyridine-5-carbonyl}-3-(3-isopropoxy-phenyl)urea,
1-{1,3-dimethyl-6-[2-(pyrrolidin-1-yl)ethyl]-1H-pyrazolo[3,4-b]pyridine-5 5-carbonyl}-3-(3-isopropoxy-phenyl)urea,
1-{1,3-dimethyl-6-[2-(piperidin-1-yl)ethyl]-1H-pyrazolo[3,4-b]pyridine-5 5-carbonyl}-3-(3-isopropoxy-phenyl)urea,
1-{1,3-dimethyl-6-[2-(morpholin-4-yl)ethyl]-1H-pyrazolo[3,4-b]pyridine-5-carbonyl}-3-(3-isopropoxy-phenyl)urea,
1-{1,3-dimethyl-6-[2-(4-methylpiperazin-1-yl)ethyl]-1H-pyrazolo[3,4-b]pyridine-5-carbonyl}-3-(3-isopropoxy-phenyl)urea,
and their pharmaceutically acceptable salts.

Preferred compounds are:
1-{1,3-dimethyl-6-[2-(pyrrolidin-1-yl)ethoxy]-1H-pyrazolo[3,4-b]pyridine-5-carbonyl}-3-(3-isopropoxy-phenyl)urea,
1-{1,3-dimethyl-6-[2-(piperidin-1-yl)ethoxy]-1H-pyrazolo[3,4-b]pyridine-5-carbonyl}-3-(3-isopropoxy-phenyl)urea, 1-{1,3-dimethyl-6-[[2-(piperidin-1-yl)ethyl]methylamino]-1H-pyrazolo[3,4-b]pyridine-5-carbonyl}-3-(3-isopropoxy-phenyl)urea, 1-{1,3-dimethyl-6-[4-(dimethylamino)piperidin-1-yl]-1H-pyrazolo[3,4-b]pyridine-5-carbonyl}-3-(3-isopropoxy-phenyl)urea, 1-{1,3-dimethyl-6-[2-(pyrrolidin-1-ylmethyl)pyrrolidin-1-yl]-1H-pyrazolo[3,4-b]pyridine-5-carbonyl}-3-(3-isopropoxy-phenyl)urea, 1-{1,3-dimethyl-6-[2-(pyrrolidin-1-yl)ethyl]-1H-pyrazolo[3,4-b]pyridine-5pyridine-5-carbonyl}-3-(3-isopropoxy-phenyl)urea, 1-{1,3-dimethyl-6-[2-(piperidin-1-yl)ethyl]-1H-pyrazolo[3,4-b]pyridine-5-carbonyl}-3-(3-isopropoxy-phenyl)urea, 1-{1,3-dimethyl-6-[2-(4-methylpiperazin-1-yl)ethyl]-1H-pyrazolo[3,4-b]pyridine-5-carbonyl}-3-(3-isopropoxy-phenyl)urea, and their pharmaceutically acceptable salts.

A particularly preferred compound is 1-{1,3-dimethyl-6-[2-(pyrrolidin-1-yl)ethoxy]-1H-pyrazolo[3,4-b]pyridine-5-carbonyl}-3-(3-isopropoxyphenyl)urea and its pharmaceutically acceptable salts; especially a pharmaceutically acceptable salt of 1-{1,3-dimethyl-6-[2-(pyrrolidin-1-yl)ethoxy]-1H-pyrazolo[3,4-b]pyridine-5-carbonyl}-3-(3-isopropoxyphenyl)urea, such as the hydrochloride salt.

The following general procedures may be employed for the preparation of the compounds of the present invention.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such references as Fieser and Fieser's *Reagents for Organic Synthesis*, vols. 1–17, John Wiley and Sons, New York, N.Y., 1991; *Rodd's Chemistry of Carbon Compounds*, vols. 1–5 and supps., Elsevier Science Publishers, 1989; Organic Reactions, vols. 1–40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. For example, suitable protective groups for amino, hydroxy, and carboxy groups are described in Greene et al., *Protective Groups in Organic Synthesis*, Second Edition, John Wiley and Sons, New York, 1991. Activation of carboxylic acids can be achieved by using a number of different reagents as described in Larock: *Comprehensive Organic Transformations*, VCH Publishers, New York, 1989.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

A suitable general synthetic route to the compounds of this invention is shown below.

In the first step(s), 6-hydroxy-1,3-dimethylpyrazolo[5,4-b]pyridine-5-carbonitrile (i) is formed by the reaction of 5-amino-1,3-dimethylpyrazole-4-carboxaldehyde and an alkyl cyanoacetate (ethyl cyanoacetate is shown). This may be converted to the corresponding carboxamide (iii) by hydrolysis with a reagent such as concentrated sulfuric acid; or the hydroxyl group may be converted to a chlorine by reaction with a chlorinating agent such as phenylphosphonic dichloride, giving 6-hydroxy-1,3-dimethylpyrazolo[5,4-b]pyridine-5-carbonitrile (ii), and that may be converted to the corresponding carboxamide (iv) by the same method as for (ii).

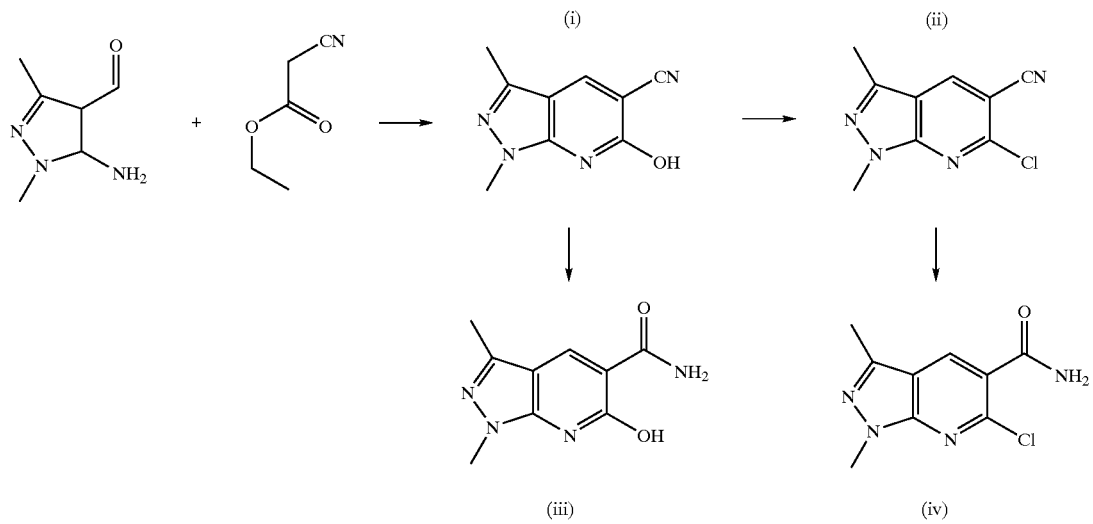

The compounds of formula A where X is O may then be prepared in a first method by reacting compounds (i) or (iii) with an ω-haloalkyl(cycloamine) (a chloroalkylamine is shown) and base, converting the nitrile to the carboxamide if compound (i) was initially used, and then reacting the carboxamide with 3-isopropoxyphenyl isocyanate. The resulting compounds of formula A may be isolated as the free base, or as a salt, especially a pharmaceutically acceptable salt.

NH, or N(CH$_3$) may be prepared, by reacting compounds (ii) or (iv) with an ω-hydroxyalkyl(cycloamine), ω-aminoalkyl (cycloamine), or ω-methylaminoalkyl(cycloamine), optionally in the presence of a base, converting the nitrile to the carboxamide if compound (ii) was initially used, and then reacting the carboxamide with 3-isopropoxyphenyl isocyanate. The resulting compounds of formula A may be isolated as the free base, or as a salt, especially a pharmaceutically acceptable salt.

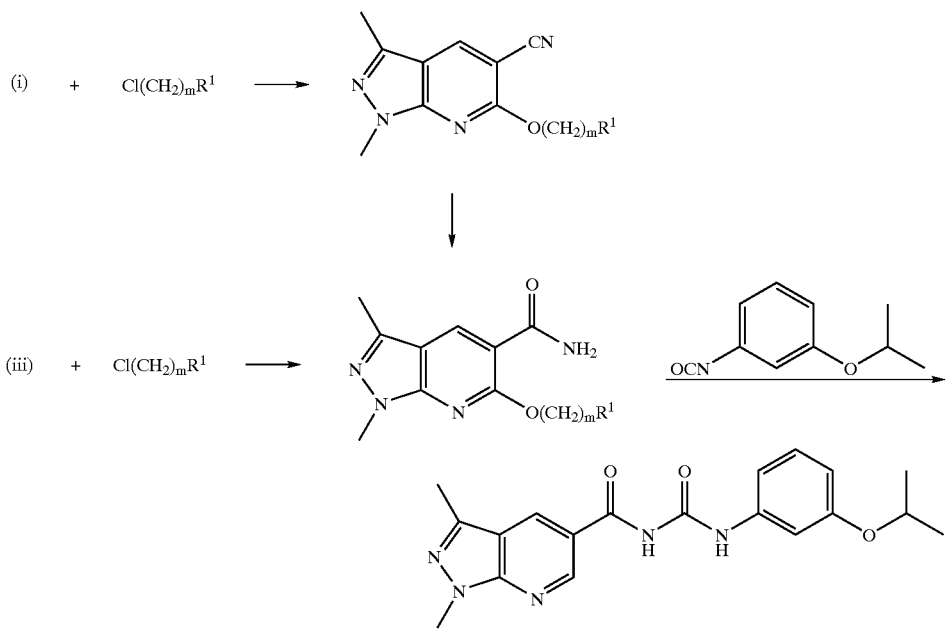

Compounds of formula A where X is O may be prepared by a second method, compounds of formula A where X is

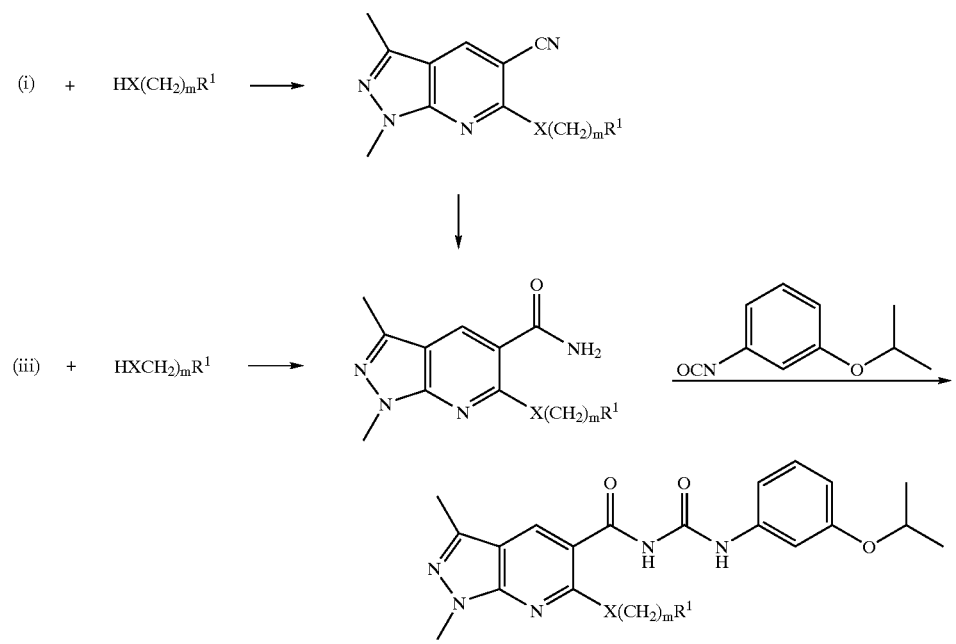

Compounds of formula B may be similarly prepared by reacting compounds (ii) or (iv) with a an appropriate cyclic amine, optionally in the presence of a base, converting the nitrile to the carboxamide if compound (ii) was initially used, and then reacting the carboxamide with 3-isopropoxyphenyl isocyanate. The resulting compounds of formula B may be isolated as the free base, or as a salt, especially a pharmaceutically acceptable salt.

Compounds of formula A where X is $CH_2$ may be prepared by reacting compounds (ii) or (iv) with a vinyl-stannane in the presence of a palladium catalyst (Stille coupling) to form the appropriate 6-vinyl compound, reacting that with an amine in the presence of a weak acid, converting the nitrile to the carboxamide if compound (ii) was initially used, and then reacting the carboxamide with 3-isopropoxyphenyl isocyanate. The resulting compounds of formula A may be isolated as the free base, or as a salt, especially a pharmaceutically acceptable salt.

The carboxamide and the isocyanate may be combined as solutions or suspensions, depending on the solubilities of the compounds in the selected solvent. The carboxamide and the isocyanate may be added in a stoichiometric ratio (1:1), or a slight excess of the isocyanate may be used, for example between 1.01 fold and 2 fold excess, but typically about 1.01 to about 1.2 fold excess. Typically, the isocyanate is added to a suspension of the carboxamide in toluene, and the resulting mixture is heated until the reaction is determined to be complete. The reaction mixture may be heated at about 10° C. to about 150° C., preferably at about 40° C. to about 120° C., e.g. under an inert atmosphere such as nitrogen, or the reaction mixture may be maintained at its reflux temperature. The reaction may be allowed to proceed to completion in about 10 minutes to 24 hours. Preferably, the reaction is heated to reflux until the reaction is complete, over about 6 to 24 hours.

The compounds may also be prepared from the condensation of the carboxamide with 3-isopropoxyaniline. In the

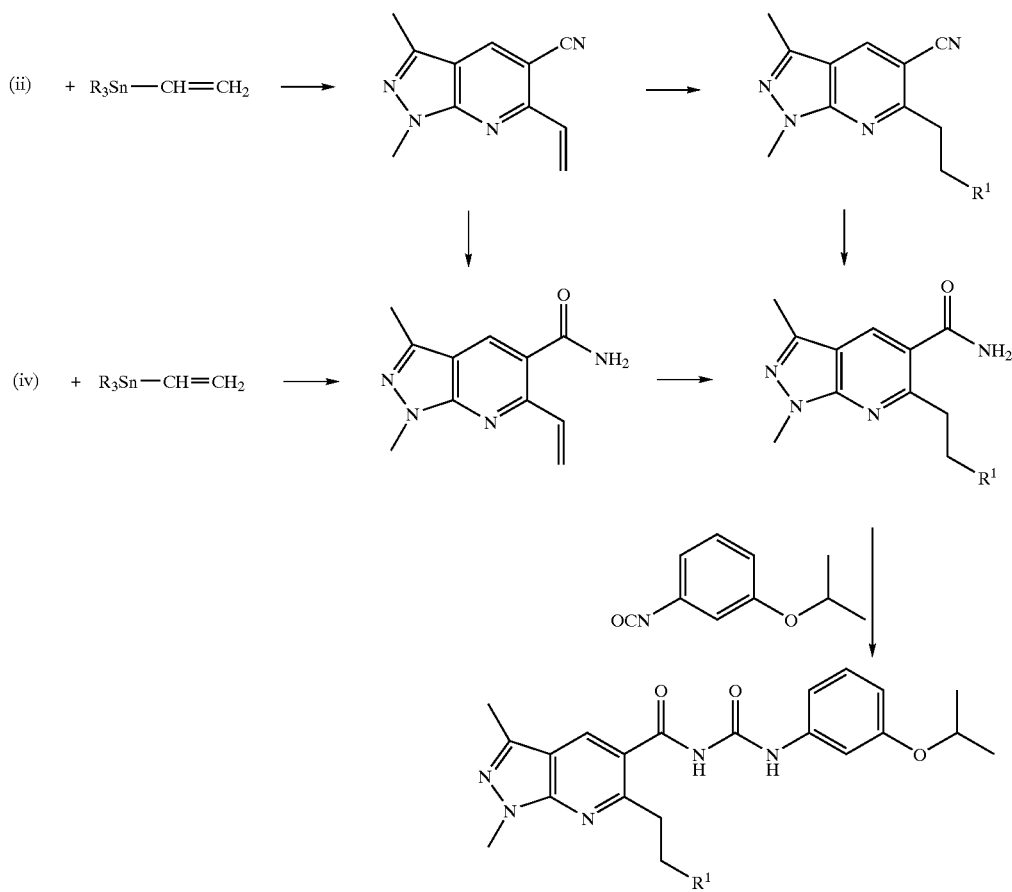

Some of these methods are illustrated in the Preparations, Reference Example, and Examples 1–17 below.

It will be evident to a person of ordinary skill in the art that variations will be possible on these methods, for example, a carboxamide may be reacted with the 3-isopropoxyphenyl isocyanate before the 6-position sidechain is added, the reaction with 3-isopropoxyphenyl isocyanate may be replaced by reaction with a haloformylation reagent such as oxalyl chloride followed by reaction with 3-isopropoxyaniline, etc.

Typically, the carboxamide is treated with the isocyanate in an organic solvent or solvent mixture, such as toluene.

first step of this process, the carboxamide in a suitable aprotic solvent is treated with a haloformylation reagent to form the corresponding carboxamide carbonylchloride derivative. Typically, the aprotic solvent is dichloromethane, toluene, tetrahydrofuran, or 2-methyl-tetrahydrofuran, preferably tetrahydrofuran, and the haloformylation reagent is oxalyl chloride, preferably present in an excess, for example between 1.1 to 3.0 equivalents, typically about 1.5 equivalents over the carboxamide. The reaction is generally performed under an inert atmosphere where the mixture is heated to 50° C. to 175° C. for 15 minutes to 24 hours until the reaction is complete. Typically, the reaction is heated to reflux over 2 to 16 hours under nitrogen, and then cooled to room temperature. The solvent is removed under vacuum, and the resulting carboxamide carbonylchloride is then condensed with the 3-isopropoxyaniline. Condensation with the 3-isopropoxyaniline may be performed by the addition of a solution of the 3-isopropoxyanaline in an aprotic solvent, such as THF, under an inert atmosphere, at a temperature between 0° C. and 20° C., preferably between 0° C. and 5°C., for 1 to 24 hours, until the reaction is complete. If the haloformylation and the subsequent condensation reaction is performed in the same solvent, the intermediate solvent removal step may be eliminated.

Upon cooling of the reaction mixture, the resulting compound of this invention may be isolated and purified by conventional techniques. Typically, the product precipitates and is isolated by filtration. Optionally, the compounds prepared according to this procedure may be converted to the corresponding pharmaceutically acceptable salts either prior to or subsequent to isolation and/or purification.

Pharmaceutical Compositions

In a second aspect, this invention is pharmaceutical compositions comprising a compound of the first aspect of this invention, typically a therapeutically effective amount, and a pharmaceutically acceptable excipient.

Pharmaceutical compositions containing compounds of this invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable excipients are normal isotonic saline solution, 5% dextrose in water or buffered sodium or ammonium acetate solution. Such formulations are especially suitable for parenteral administration but may also be used for oral administration. It may be desirable to add excipients such as povidone, gelatin, hydroxypropylcellulose, acacia, polyethylene glycol, mannitol, sodium chloride, or sodium citrate.

Alternatively, and desirably, the compounds may be encapsulated, tableted, or prepared in a solution, suspension, emulsion, or syrup for oral administration. Pharmaceutically acceptable solid or liquid excipients may be added to enhance or stabilize the composition, or to facilitate preparation of the composition. Liquid excipients include syrup, peanut oil, olive oil, glycerin, saline, alcohols, or water. Solid excipients include starch, lactose, calcium sulfate dihydrate, terra alba, magnesium stearate or stearic acid, talc, pectin, acacia, agar, or gelatin. The excipient may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing, and filling for hard gelatin capsule forms. When a liquid excipient is used, the preparation will be in the form of a syrup, elixir, emulsion, or an aqueous or non-aqueous suspension. Such a liquid formulation may be administered directly p.o. or filled into a soft gelatin capsule.

Some specific examples of suitable pharmaceutical compositions are described in Examples 19–21 below.

Typically, a pharmaceutical composition of this invention is packaged in a container with a label or package insert indicating the use of the pharmaceutical composition in the treatment of a chronic or acute inflammatory or autoimmune disease, especially those associated with aberrant lymphocyte or monocyte accumulation such as atherosclerosis, Crohn's disease, diabetic nephropathy, inflammatory bowel disease, multiple sclerosis, nephritis, pancreatitis, pulmonary fibrosis, psoriasis, restenosis, rheumatoid arthritis, and transplant rejection, or an allergic hypersensitivity disorder, such as allergic rhinitis and asthma.

Methods of Use

In a third aspect, this invention is a method for treating, in a mammal in need thereof, a disease treatable by administration of an MCP-1 inhibitor, comprising administering to the mammal a therapeutically effective amount of a compound of the first aspect of this invention. Exemplary diseases treatable by the compounds of this invention include inflammatory and autoimmune diseases such as atherosclerosis, Crohn's disease, diabetic nephropathy, inflammatory bowel disease, multiple sclerosis, nephritis, pancreatitis, pulmonary fibrosis, psoriasis, restenosis, rheumatoid arthritis, and transplant rejection; and allergic hypersensitivity disorders such as allergic rhinitis and asthma.

The compounds of this invention inhibit chemotaxis of a human monocytic cell line (THP-1 cells) induced by human MCP-1 in vitro; and one has been shown to be extremely potent in the experimental allergic encephalomyelitis model of multiple sclerosis.

Related compounds (those of U.S. application Ser. No. 10/060,967) have shown the same inhibitory effect on MCP-1-induced chemotaxis, and similar effects in vivo, have shown reduction of monocyte infiltration in a thioglycolate-induced inflammation model in mice, and have been found to prevent the onset or ameliorate symptoms in several animal models of inflammation. For example, such compounds inhibited recruitment of monocytes into the glomeruli in an anti-Thy-1 antibody-induced model of nephritis; reduced paw swelling in a rat model of adjuvant arthritis; inhibited neointimal hyperplasia after balloon injury in a rat model of restenosis, and reduced the amount of lesion of the aortic sinus in an apoE-deficient mouse model of atherosclerosis.

The use of the compounds of the invention for treating inflammatory and autoimmune disease by combination therapy may also comprise the administration of the compound of the invention to a mammal in combination with common anti-inflammatory drugs, cytokines, or immunomodulators.

Suitable dosages of the compounds of this invention are 1–1000 mg/Kg, preferably 5–200 mg/Kg, and more preferably 10–100 mg/Kg, and the appropriate range for therapeutic effectiveness will be readily determined by one skilled in the art depending on the route of administration, age, and condition of the mammal being treated. These dosage units may be administered one to ten times daily for acute or chronic disease. No unacceptable toxicological effects are expected when compounds of the invention are used in accordance with the present invention.

The compounds of this invention may be administered by any route suitable to the mammal being treated and the nature of the disease. Routes of administration include, but are not limited to, administration by injection, including intravenous, intraperitoneal, intramuscular, and subcutaneous injection, by transmucosal or transdermal delivery, topically, by nasal spray, suppository and the like, or orally. Formulations may optionally be liposomal formulations, emulsions, formulations designed to administer the drug across mucosal membranes or transdermal formulations. Suitable formulations for each of these methods of administration may be found, for example, in *Remington: The Science and Practice of Pharmacy*, A. Gennaro, ed., 20th edition, Lippincott, Williams & Wilkins, Philadelphia, Pa.

This invention also includes the use of compounds of the first aspect of this invention in the preparation of medicaments for the treatment of diseases treatable by administering an antagonist of MCP-1 function.

The invention is illustrated by the following non-limiting Preparations and Examples.

Preparation 1

6-Hydroxy-1,3-dimethylpyrazolo[5,4-b]pyridine-5-carbonitrile

5-Amino-1,3-dimethylpyrazole-4-carboxaldehyde (6.15 g) was dissolved in ethyl cyanoacetate (10 mL), and stirred at 185° C. for 3 hours. The reaction mixture was allowed to cool to room temperature. The precipitated solid was filtered, washed with ethyl acetate, and dried under high vacuum to give 6-hydroxy-1,3-dimethylpyrazolo[5,4-b]pyridine-5-carbonitrile as a white powder.

Preparation 2

6-Chloro-1,3-dimethylpyrazolo[5,4-b]pyridine-5-carbonitrile

6-Hydroxy-1,3-dimethylpyrazolo[5,4-b]pyridine-5-carbonitrile (2.18 g) was dissolved in phenylphosphonic dichloride, and stirred at 150° C. for 17 hours. The solution was allowed to cool to room temperature and poured into water, then extracted with ethyl acetate. The extract was washed with saturated NaHCO$_3$ solution and dried over Na$_2$SO$_4$. Evaporation of the solvent gave 6-chloro-1,3-dimethylpyrazolo[5,4-b]pyridine-5-carbonitrile as a white solid.

EXAMPLE 1

1-{1,3-dimethyl-6-[2-(pyrrolidin-1-yl)ethoxy]-1H-pyrazolo[3,4-b]pyridine-5-carbonyl}-3-(3-isopropoxyphenyl)urea hydrochloride (1)

The overall reaction sequence is shown in the reaction scheme below:

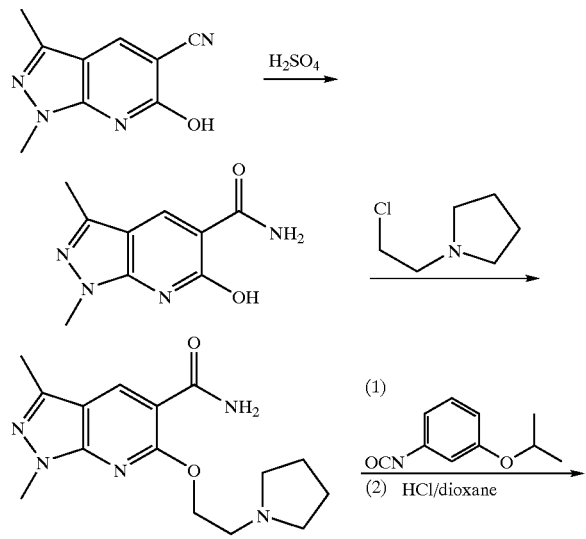

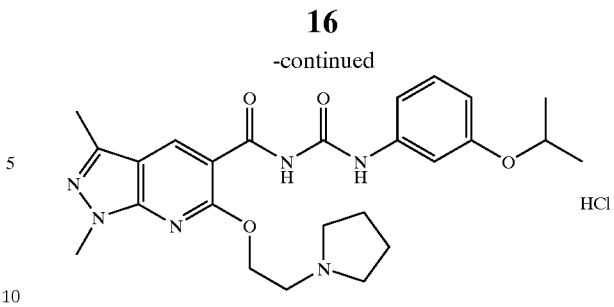

6-Hydroxy-1,3-dimethylpyrazolo[5,4-b]pyridine-5-carbonitrile (0.91 g) was dissolved in concentrated H$_2$SO$_4$ (3 mL) and stirred at 40° C. for 24 hours. The solution was poured into ice water and the precipitate was filtered, washed with water, and dried under high vacuum to give 6-hydroxy-1,3-dimethylpyrazolo[5,4-b]pyridine-5-carboxamide as a white solid. A portion of this material (0.12 g) was dissolved in DMF (2 mL) and treated with 1-(2-chloroethyl)pyrrolidine hydrochloride (0.12 g) and potassium carbonate (0.30 g). The reaction mixture was stirred at 60° C. for 18 h, poured into water, and extracted with ethyl acetate. The extract was washed with saturated NaHCO$_3$ solution and brine, dried over Na$_2$SO$_4$ and concentrated under reduced pressure to give 1,3-dimethyl-6-[2-(pyrrolidin-1-yl)-ethoxy]-1H-pyrazolo[3,4-b]pyridine-5-carboxamide. A portion of this material (0.06 g) was dissolved in toluene and treated with 3-isopropoxyphenyl isocyanate (0.1 g). The mixture was heated at reflux for 23 hours, and then cooled to room temperature. The solvent was evaporated under reduced pressure, and the residue was purified by column chromatography (methanol/ethyl acetate). A portion of this material was dissolved in tetrahydrofuran and treated with 4M HCl/dioxane. The solid material obtained was recrystallized from acetonitrile to give 1-{1,3-dimethyl-6-[2-(pyrrolidin-1-yl)ethoxy]-1H-pyrazolo[3,4-b]pyridine-5-carbonyl}-3-(3-isopropoxyphenyl)urea hydrochloride (1), as a white solid.

$^1$H NMR (DMSO-d$_6$) δ ppm: 1.3 (d, 6H), 1.8–2 (m, 4H), 2.5 (s, 3H), 3.1 (m, 2H), 3.6 (m, 4H), 3.9 (s, 3H), 4.5 (m, 1H), 4.8 (m, 2H), 6.6 (d, 1H), 7.0 (d, 1H), 7.2 (m, 2H), 8.5 (s, 1H), 10.6 (s, 1H), 10.7 (s, 1H),10.9 (brs, 1H). LCMS: m/z 481 (M+H).

EXAMPLES 2–4

Using the method of Example 1, but replacing the 1-(2-chloroethyl)pyrrolidine with 1-(2-chloroethyl)piperidine, 4-(2-chloroethyl)morpholine, and 1-(3-chloropropyl)hexahydroazepine, there were obtained 1-{1,3-dimethyl-6-[2-(piperidin-1-yl)ethoxy]-1H-pyrazolo[3,4-b]pyridine-5-carbonyl}-3-(3-isopropoxyphenyl)urea hydrochloride (2), 1-{1,3-dimethyl-6-[2-(morpholin-4-yl)ethoxy]-1H-pyrazolo[3,4-b]pyridine-5-carbonyl}-3-(3-isopropoxyphenyl)urea hydrochloride (3), and 1-{1,3-dimethyl-6-[3-(hexahydroazepin-1-yl)propoxy]-1H-pyrazolo[3,4-b]pyridine-5-carbonyl}-3-(3-isopropoxyphenyl)urea hydrochloride (4).

EXAMPLES 5–13

Using the method of Example 1, but replacing the 6-hydroxy-1,3-dimethyl-pyrazolo[5,4-b]pyridine-5-carbonitrile with 6-chloro-1,3-dimethylpyrazolo [5,4-b]pyridine-5-carbonitrile, and reacting with 1-(2-aminoethyl) pyrrolidine, there was obtained 1-{1,3-dimethyl-6-[2-(pyrrolidin-1-yl)ethylamino]-1H-pyrazolo[3,4-b]pyridine-5-carbonyl}-3-(3-isopropoxyphenyl)urea hydrochloride (5).

Using the same method, but replacing the 1-(2-aminoethyl) pyrrolidine with 1-(2-aminoethyl)piperidine, 4-(2-aminoethyl)morpholine, [2-(pyrrolidin-1-yl)ethyl] methylamine, and [2-(piperidin-1-yl)ethyl]-methylamine, there were obtained 1-{1,3-dimethyl-6-[2-(piperidin-1-yl) ethylamino]-1H-pyrazolo [3,4-b]pyridine-5-carbonyl}-3-(3-isopropoxyphenyl)urea hydrochloride (6), 1-{1,3-dimethyl-6-[2-(morpholin-4-yl)ethylamino]-1H-pyrazolo[3,4-b] pyridine-5-carbonyl}-3-(3-isopropoxyphenyl)urea hydrochloride (7), 1-{1,3-dimethyl-6-[[2-(pyrrolidin-1-yl) ethyl]methylamino]-1H-pyrazolo[3,4-b]pyridine-5-carbonyl}-3-(3-isopropoxyphenyl)urea hydrochloride (8), and 1-{1,3-dimethyl-6-[[2-(piperidin-1-yl)-methylamino]-1H-pyrazolo[3,4-b]pyridine-5-carbonyl}-3-(3-isopropoxyphenyl)urea hydrochloride (9). Using the same method, but replacing the 1-(2-aminoethyl)pyrrolidine with 4-(pyrrolidin-1-yl)-piperidine, 4-(piperidin-1-yl)piperidine, 4-(dimethylamino)piperidine, and 2-(pyrrolidin-1-ylmethyl)-pyrrolidine, there were obtained 1-{1,3-dimethyl-6-[4-(pyrrolidin-1-yl)piperidin-1-yl]-1H-pyrazolo[3,4-b] pyridine-5-carbonyl}-3-(3-isopropoxyphenyl)urea hydrochloride (10), 1-{1,3-dimethyl-6-[4-(piperidin-1-yl) piperidin-1-yl]-1H-pyrazolo[3,4-b]pyridine-5-carbonyl}-3-(3-isopropoxyphenyl)urea hydrochloride (11), 1-{1,3-dimethyl-6-[4-(dimethylamino)piperidin-1yl]-1H-pyrazolo [3,4-b]pyridine-5-carbonyl}-3-(3-isopropoxyphenyl)urea hydrochloride (12), and 1-{1,3-dimethyl-6-[2-(pyrrolidin-1-ylmethyl)pyrrolidin-1-yl]-1H-pyrazolo[3,4-b]pyridine-5-carbonyl}-3-(3-isopropoxyphenyl)urea hydrochloride (13). The compounds of Examples 1–4 may also be prepared by the same method, starting with 6-chloro-1,3-dimethylpyrazolo[5,4-b]pyridine-5-carbonitrile and using 1-(2-hydroxyethyl)pyrrolidine, 1-(2-hydroxyethyl) piperidine, 4-(2-hydroxyethyl)morpholine, and 1-(3-hydroxypropyl)hexahydroazepine.

REFERENCE EXAMPLE 1

1-{1,3-Dimethyl-6-[2-(pyrrolidin-1-yl)ethyl]-1H-pyrazolo [3,4-b]pyridine-5-carbonyl}-3-(3-isopropoxy-4-methylphenyl)urea [not a compound of this invention]

The overall reaction sequence is shown in the reaction scheme below:

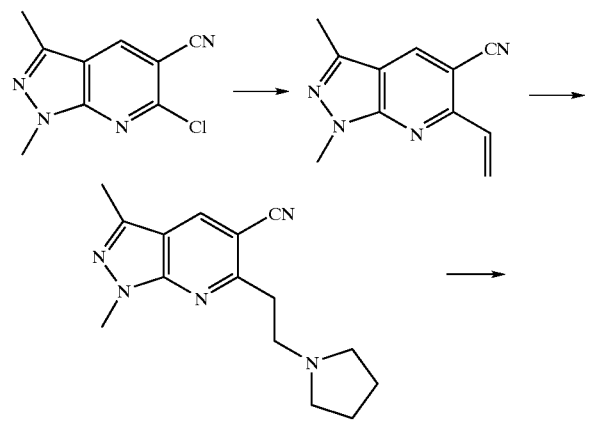

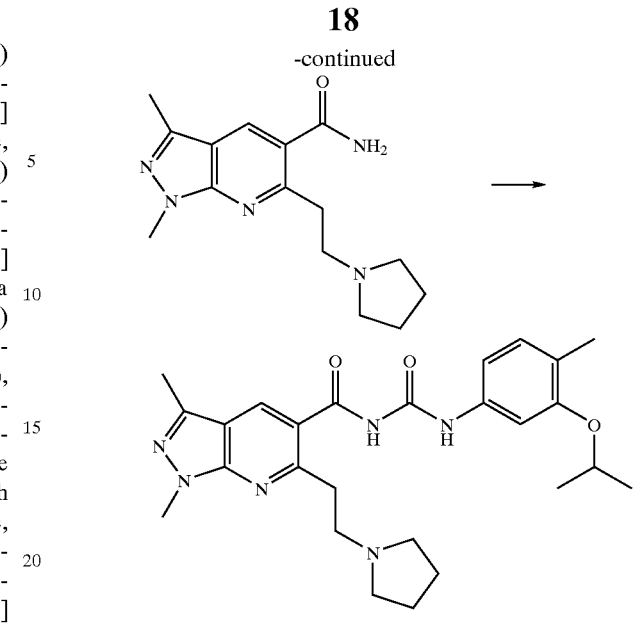

6-Chloro-1,3-dimethyl-1H-pyrazolo[3,4-b]pyridine-5-carbonitrile (2.71 g, 13.1 mmol) was dissolved in toluene (45 mL). Vinyl tributyltin (5 g, 15.8 mmol) and triphenylphosphine (103 mg, 3.93 mmol) were added, followed by $Pd(PPh_3)_4$ (151 mg, 0.13 mmol). The reaction mixture was heated at reflux for 2 hours, allowed to cool to room temperature, and then treated with saturated aqueous KF solution for 30 minutes. The precipitated solid (tributyltin fluoride) was removed by filtration. The aqueous layer was separated and extracted with ethyl acetate. The combined organic layers were dried over $Na_2SO_4$ and concentrated under reduced pressure. The residue was washed with hexane to give 1,3-dimethyl-6-vinyl-1H-pyrazolo[3,4-b] pyridine-5-carbonitrile (2.50 g, 96%) as a pale yellow powder.

A solution of 1,3-dimethyl-6-vinyl-1H-pyrazolo[3,4-b] pyridine-5-carbonitrile (2.20 g, 11.1 mmol) in methanol (110 mL) was treated with acetic acid (635 μL, 11.1 mmol) and pyrrolidine (4.59 mL, 55.5 mmol). The mixture was stirred at room temperature for 3 hours and the solvent removed under reduced pressure. The residue was suspended in water and extracted with ethyl acetate. The combined organic layers were dried over $Na_2SO_4$ and concentrated to give 1,3-dimethyl-6-[2-(pyrrolidin-1-yl)ethyl]-1H-pyrazolo[3,4-b]pyridine-5-carbonitrile as a tan solid.

1,3-Dimethyl-6-[2-(pyrrolidin-1-yl)ethyl]-1H-pyrazolo [3,4-b]pyridine-5-carbonitrile was dissolved in concentrated $H_2SO_4$ (55 mL) and the solution stirred at 60° C. for 2 days. The mixture was cooled to 0° C., treated with 6N NaOH to pH 14, and extracted with ethyl acetate. The organic extract was evaporated under reduced pressure and the residue washed with ether to give 1,3-dimethyl-6-[2-(pyrrolidin-1-yl)ethyl)-1H-pyrazolo [3,4-b]pyridine-5-carboxamide (2.5 g).

1,3-Dimethyl-6-[2-(pyrrolidin-1-yl)ethyl)-1H-pyrazolo [3,4-b]pyridine-5-carboxamide (120 mg) was suspended in toluene (20 mL). 3-Isopropoxy-4-methylphenyl isocyanate (100 mg) was added and the solution refluxed under nitrogen for 18 hours. After cooling, the precipitated solid was filtered and the filtrate concentrated to give crude 1-{1,3-dimethyl-6-[2-(pyrrolidin-1-yl)ethyl]-1H-pyrazolo[3,4-b] pyridine-5-carbonyl}-3-(3-isopropoxy-4-methyl-phenyl) urea, which was purified by HPLC to give the final product as the trifluoroacetate salt (3.3 mg). MS (ESI+) m/z 497 (M+H).

EXAMPLES 14–17

Using the method of Reference Example 1, but replacing the 3-isopropoxy-4-methylphenyl isocyanate with 3-isopropoxyphenyl isocyanate, there was obtained 1-{1,3-dimethyl-6-[2-(pyrrolidin-1-yl)ethyl]-1H-pyrazolo[3,4-b]pyridine-5-carbonyl}-3-(3-isopropoxyphenyl)urea hydrochloride (14). Using the same method, but replacing the pyrrolidine with piperidine, morpholine, and 1-methylpiperazine, there were obtained 1-{1,3-dimethyl-6-[2-(piperidin-1-yl)ethyl]-1H-pyrazolo[3,4-b]pyridine-5-carbonyl}-3-(3-isopropoxyphenyl)urea hydrochloride (15), 1-{1,3-dimethyl-6-[2-(morpholin-4-yl)-ethyl]-1H-pyrazolo[3,4-b]pyridine-5-carbonyl}-3-(3-isopropoxyphenyl)urea hydrochloride (17), and 1-{1,3-dimethyl-6-[2-(4-methylpiperazin1-yl)ethyl]-1H-pyrazolo[3,4-b]pyridine-5-carbonyl}-3-(3-isopropoxyphenyl)urea hydrochloride (17).

EXAMPLE 18

Inhibition of MCP-1 Induced Chemotaxis

A 48-well microchemotaxis chamber with a 5 µm pore size, PVP-coated polycarbonate filter membrane (Neuro Probe Inc., Cabin John, Md.) was used for testing. Compounds were prepared as 10 mM stock solution in DMSO. THP-1 cells were washed with RPMI 1640 medium supplemented with 0.5% BSA and 25 mM HEPES, pH 7.4, and suspended at a density of $4 \times 10^6$ cells/mL in the same medium. A 150 µL aliquot of this suspension was treated with an equal volume of test compound solution and the mixture incubated at 37° C. for 15 minutes. The lower chamber was loaded with 26 µL of a 2.5 nM solution of hMCP-1 (PeproTech) in medium. The filter membrane was placed over the lower chamber, followed by a silicone rubber gasket and the upper chamber. A 50 µL aliquot of the THP-1 cell suspension containing the test compound was added to the upper chamber and the assembly incubated in a 5% $CO_2$ atmosphere at 37° C. for 2 hours. The chamber was then disassembled and the cells remaining on the upper surface of the filter were scraped off with a rubber scraper. The filter was fixed with methanol, stained with Diff-Quik solution, and mounted on a glass slide. The cells that had migrated across the filter onto the lower surface were then counted by microscopic observation. The table shows the $IC_{50}$ (concentration of compound that inhibited migration of 50% of the cells relative to control) for several compounds of the present invention.

Selected Compounds on MCP-1-Induced Chemotaxis

| Compound | $IC_{50}$ (µM) |
|---|---|
| 1 | 0.07 |
| 2 | 0.22 |
| 4 | 1.8 |
| 5 | 0.25 |
| 6 | 1.2 |
| 7 | 0.8 |
| 8 | 0.4 |
| 9 | 4.6 |
| 10 | 0.06 |
| 11 | 10 |
| 12 | 1 |
| 13 | 0.16 |
| 14 | 0.08 |
| 15 | 0.07 |
| 16 | 7.5 |
| 17 | 2.2 |

EXAMPLE 18

Experimental Allergic Encephalomyelitis (EAE) Model of Multiple Sclerosis

EAE was induced in two groups, each of 10 mice, by subcutaneous injection into the flank of 150 µg of the encephalitogenic peptide $MOG_{35-55}$ (MEVGWYRSPFSRVVHLYRNGK; Auspep, Melbourne, Australia) emulsified in complete Freund's adjuvant (Difco, Detroit, U.S.A.), supplemented with 4 mg/mL of *Mycobacterium tuberculosis*, followed by intravenous injection of 350 ng of pertussis vaccine (List Biological Laboratories, Campbell, U.S.A.), with the pertussis vaccine injection repeated after 48 hours.

Compound 1 was dissolved in 3% aqueous Tween 80 at 4mg/mL and stored at 4° C. Starting on the day of immunization with $MOG_{35-55}$, the mice were treated twice daily with 30 mg/Kg of compound 1 or an equal volume of water for the 35 day duration of the experiment.

The mice were monitored daily and neurological impairment was quantified on an arbitrary scale: 0, no detectable impairment; 1, flaccid tail; 2, hind limb weakness; 3, hind limb paralysis; 4, hind limb paralysis and ascending paralysis; 5, moribund or dead.

At the end of the experiment, the mice were killed and hematoxylin and eosin stained sections of brain and spinal cord were scored blindly by two independent investigators using the following scale: 0, no inflammation; 1, few very small cellular infiltrate in the perivascular areas and meninges; 2, mild cellular infiltrate; 3, moderate cellular infiltrate; 4, severe cellular infiltrate; 5, very large and extensive cellular infiltrate.

| Effect of Compound 1 on EAE | | | |
|---|---|---|---|
| Measure | Compound 1 | Control | Significance (p value) |
| EAE incidence | 5/10 | 10/10 | ≦0.01 (c2 test) |
| Mean onset (days) | 17.2 | 13.3 | 0.0013 (Mann-Whitney test) |
| Mean maximum score | 1.4 | 3.9 | 0.0003 (Mann-Whitney test) |
| Mean cumulative score | 7.25 | 70.55 | 0.0001 (Mann-Whitney test) |

EXAMPLE 19

Oral Pharmaceutical Composition—Solid Dosage Formulation

A pharmaceutical composition for oral administration may be prepared by combining the following:

| Ingredient | % w/w |
| --- | --- |
| Compound of this invention | 10.0 |
| Magnesium stearate | 0.5 |
| Starch | 2.0 |
| Hydroxypropyl methylcellulose | 1.0 |
| Microcrystalline cellulose | 86.5 |

The mixture may be compressed into tablets, or filled into hard gelatin capsules. The tablet may be coated by applying a suspension of a film former (e.g., hydroxypropyl methylcellulose), pigment (e.g., titanium dioxide) and plasticizer (e.g., diethyl phthalate) and drying the film by evaporation of the solvent. The film coat can comprise 2.0% to 6.0% of the tablet weight, preferably about 3.0%.

EXAMPLE 20

Oral Pharmaceutical Composition—Softgel Capsule

A pharmaceutical composition of a compound of the invention suitable for oral administration may also be prepared by combining the following:

| Ingredient | % w/w |
| --- | --- |
| Compound of this invention | 20 |
| Polyethylene glycol 400 | 80 |

The compound is dispersed or dissolved in the liquid carrier, with a thickening agent added, if required. The formulation is then enclosed in a soft gelatin capsule by suitable technology.

EXAMPLE 21

Parenteral Pharmaceutical Composition

A pharmaceutical composition for parenteral administration may be prepared by combining the following:

| Ingredient | % w/w |
| --- | --- |
| Compound of this invention | 1.0 |
| Saline | 99.0 |

The solution is sterilized and sealed in sterile containers.

Various modifications and variations of the present invention will be apparent to those skilled in the art without departing from the scope and spirit of the invention. Although the invention has been described in connection with specific preferred embodiments, it should be understood that the invention as disclosed should not be unduly limited to such specific embodiments. Various modifications of the described modes for carrying out the invention which are obvious to those skilled in the art are intended to be within the scope of this invention.

We claim:

1. A compound selected from the group consisting of compounds of formula A and formula B:

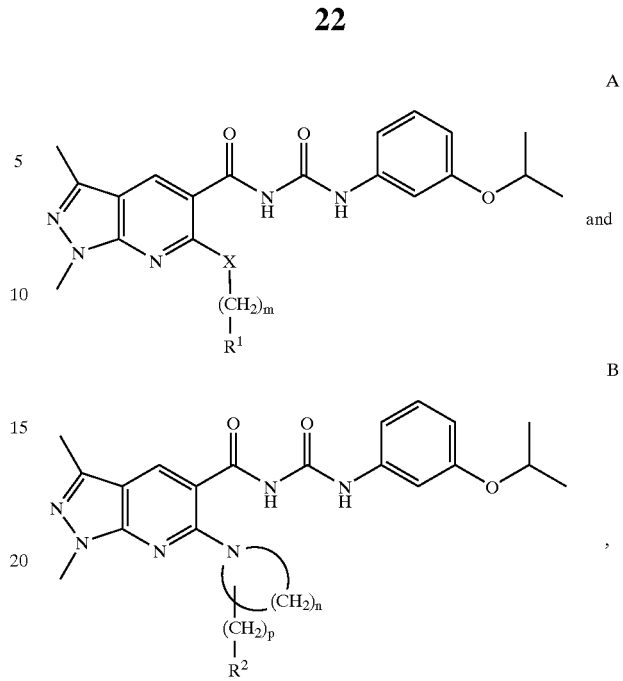

where:
m is 1, 2, or 3 (except that when X is $CH_2$, m is 1);
n is 4 or 5;
p is 0 or 1;
$R^1$ is pyrrolidin-1-yl, piperidin-1-yl, morpholin-4-yl, piperazin-1-yl, 4-methylpiperazin-1-yl, or hexahydroazepin-1-yl;
$R^2$ is dimethylamino, ethylmethylamino, diethylamino, pyrrolidin-1-yl, or piperidin-1-yl;
X is O, $CH_2$, NH, or $N(CH_3)$,
and their pharmaceutically acceptable salts.

2. The compound of claim 1 that is selected from the group consisting of compounds of formula A and their pharmaceutically acceptable salts.

3. The compound of claim 2 where X is O.

4. The compound of claim 3 where m is 2.

5. The compound of claim 2 where X is NH or $N(CH_3)$.

6. The compound of claim 5 where m is 2.

7. The compound of claim 2 where X is $CH_2$.

8. The compound of claim 1 that is selected from the group consisting of compounds of formula B and their pharmaceutically acceptable salts.

9. The compound of claim 8 where n is 5.

10. The compound of claim 9 where p is 0.

11. The compound of claim 1 that is selected from the group consisting of:
1-{1,3-dimethyl-6-[2-(pyrrolidin-1-yl)ethoxy]-1H-pyrazolo[3,4-b]pyridine-5-carbonyl}-3-(3-isopropoxyphenyl)urea,
1-{1,3-dimethyl-6-[2-(piperidin-1-yl)ethoxy]-1H-pyrazolo[3,4-b]pyridine-5-carbonyl}-3-(3-isopropoxyphenyl)urea,
1-{1,3-dimethyl-6-[2-(morpholin-4-yl)ethoxy]-1H-pyrazolo[3,4-b]pyridine-5-carbonyl}-3-(3-isopropoxyphenyl)urea,
1-{1,3-dimethyl-6-[3-(hexahydroazepin-1-yl)propoxy]-1H-pyrazolo[3,4-b]pyridine-5-carbonyl}-3-(3-isopropoxyphenyl)urea,
1-{1,3-dimethyl-6-[2-(pyrrolidin-1-yl)ethylamino]-1H-pyrazolo[3,4-b]pyridine-5-carbonyl}-3-(3-isopropoxyphenyl)urea, 1-{1,3-dimethyl-6-[2-(piperidin-1-yl)ethylamino]-1H-pyrazolo[3,4-b]pyridine-5-carbonyl}-3-(3-isopropoxyphenyl)urea, 1-{1,3-dimethyl-6-[2-(morpholin-4-yl)ethylamino]-1H-pyrazolo[3,4-b]pyridine-5-carbonyl}-3-(3-isopropoxyphenyl)urea, 1-{1,3-dimethyl-6-[[2-(pyrrolidin-1-yl)ethyl]methylamino]-1H-pyrazolo[3,4-b]pyridine-5--carbonyl}-3-(3-isopropoxyphenyl)urea, 1-{1,3-dimethyl-6-[[2-(piperidin-1-yl)ethyl]methylamino]-1H-pyrazolo[3,4-b]pyridine-5--carbonyl}-3-(3-isopropoxyphenyl)urea, 1-{1,3-dimethyl-6-[4-(pyrrolidin-1-yl)piperidin-1-yl]-1H-pyrazolo[3,4-b]pyridine-5--carbonyl}-3-(3-isopropoxyphenyl)urea, 1-{1,3-dimethyl-6-[4-(piperidin-1-yl)piperidin-1-yl]-1H-pyrazolo[3,4-b]pyridine-5--carbonyl}-3-(3-isopropoxyphenyl)urea, 1-{1,3-dimethyl-6-[4-(dimethylamino)piperidin-1-yl]-1H-pyrazolo[3,4-b]pyridine-5-carbonyl}-3-(3-isopropoxyphenyl)urea, 1-{1,3-dimethyl-6-[2-(pyrrolidin-1-ylmethyl)pyrrolidin-1-yl]-1H-pyrazolo[3,4-b]pyridine-5--carbonyl}-3-(3-isopropoxyphenyl)urea, 1-{1,3-dimethyl-6-[2-(pyrrolidin-1-yl)ethyl]-1H-pyrazolo[3,4-b]pyridine-5-carbonyl}-3-(3-isopropoxyphenyl)urea, 1-{1,3-dimethyl-6-[2-(piperidin-1-yl)ethyl]-1H-pyrazolo[3,4-b]pyridine-5-carbonyl}-3-(3-isopropoxyphenyl)urea, 1-{1,3-dimethyl-6-[2-(morpholin-4-yl)ethyl]-1H-pyrazolo[3,4-b]pyridine-5-carbonyl}-3-(3-isopropoxyphenyl)urea, 1-{1,3-dimethyl-6-[2-(4-methylpiperazin-1-yl)ethyl]-1H-pyrazolo[3,4-b]pyridine-5--carbonyl}-3-(3-isopropoxyphenyl)urea, and their pharmaceutically acceptable salts.

12. The compound of claim 11 that is selected from the group consisting of:

1-{1,3-dimethyl-6-[2-(pyrrolidin-1-yl)ethoxy]-1H-pyrazolo[3,4-b]pyridine-5-carbonyl}-3-(3-isopropoxyphenyl)urea, 1-{1,3-dimethyl-6-[2-(piperidin-1-yl)ethoxy]-1H-pyrazolo[3,4-b]pyridine-5-carbonyl}-3-(3-isopropoxyphenyl)urea, 1-{1,3-dimethyl-6-[[2-(piperidin-1-yl)ethyl]methylamino]-1H-pyrazolo[3,4-b]pyridine-5--carbonyl}-3-(3-isopropoxyphenyl)urea, 1-{1,3-dimethyl-6-[4-(dimethylamino)piperidin-1-yl]-1H-pyrazolo[3,4-b]pyridine-5-carbonyl}-3-(3-isopropoxyphenyl)urea, 1-{1,3-dimethyl-6-[2-(pyrrolidin-1-ylmethyl)pyrrolidin-1-yl]-1H-pyrazolo[3,4-b]pyridine-5--carbonyl}-3-(3-isopropoxyphenyl)urea, 1-{1,3-dimethyl-6-[2-(pyrrolidin-1-yl)ethyl]-1H-pyrazolo[3,4-b]pyridine-5-carbonyl}-3-(3-isopropoxyphenyl)urea, 1-{1,3-dimethyl-6-[2-(piperidin-1-yl)ethyl]-1H-pyrazolo[3,4-b]pyridine-5-carbonyl}-3-(3-isopropoxyphenyl)urea, 1-{1,3-dimethyl-6-[2-(4-methylpiperazin-1-yl)ethyl]-1H-pyrazolo[3,4-b]pyridine-5--carbonyl}-3-(3-isopropoxyphenyl)urea, and their pharmaceutically acceptable salts.

13. The compound of claim 12 that is 1-{1,3-dimethyl-6-[2-(pyrrolidin-1-yl)ethoxy]-1H-pyrazolo[3,4-b]pyridine-5-carbonyl}-3-(3-isopropoxyphenyl)urea or a pharmaceutically acceptable salt thereof.

14. The compound of claim 13 that is a pharmaceutically acceptable salt of 1-{1,3-dimethyl-6-[2-(pyrrolidin-1-yl)ethoxy]-1H-pyrazolo[3,4-b]pyridine-5-carbonyl}-3-(3-isopropoxyphenyl)urea.

15. A pharmaceutical composition comprising a compound of claim 1 and a pharmaceutically acceptable excipient.

16. A pharmaceutical composition comprising a compound of claim 13 and a pharmaceutically acceptable excipient.

17. A method of treating, in a mammal in need thereof, a disease treatable by administering an antagonist of MCP 1 function, where the disease is selected from the group consisting of: atherosclerosis, Crohn's disease, diabetic nephropathy, inflammatory bowel disease, multiple sclerosis, nephritis, pancreatitis, pulmonary fibrosis, psoriasis, restenosis, rheumatoid arthritis, transplant rejection, allergic rhinitis, and asthma, comprising administering to the mammal a therapeutically effective amount of a compound of claim 1.

18. The method of claim 17 where the disease is multiple sclerosis.

19. The method of claim 17 where the compound is 1-{1,3-dimethyl-6-[2-(pyrrolidin-1-yl)ethoxy]-1-H-pyrazolo[3,4-b]pyridine-5-carbonyl}-3-(3-isopropoxyphenyl)urea or a pharmaceutically acceptable salt thereof.

20. The method of claim 18 where the compound is 1-{1,3-dimethyl-6-[2-(pyrrolidin-1-yl)ethoxy]-1-H-pyrazolo[3,4-b]pyridine-5-carbonyl}-3-(3-isopropoxyphenyl)urea or a pharmaceutically acceptable salt thereof.

* * * * *